(12) United States Patent
Genicot et al.

(10) Patent No.: US 11,701,015 B2
(45) Date of Patent: Jul. 18, 2023

(54) COMPUTER-IMPLEMENTED METHOD AND SYSTEM FOR DIRECT PHOTOPLETHYSMOGRAPHY (PPG) WITH MULTIPLE SENSORS

(71) Applicant: QOMPIUM, Hasselt (BE)

(72) Inventors: Matthieu Genicot, Leuven (BE); Amaury Vanvinckenroye, Braives (BE); Kobe Leysen, Bilzen (BE); Lars Grieten, Zutendaal (BE); Jo Van Der Auwera, Meerhout (BE); Bieke Van Gorp, Kasterlee (BE)

(73) Assignee: QOMPIUM, Hasselt (BE)

( * ) Notice: Subject to any disclaimer, the term of this patent is extended or adjusted under 35 U.S.C. 154(b) by 212 days.

(21) Appl. No.: 16/754,313

(22) PCT Filed: Aug. 10, 2018

(86) PCT No.: PCT/EP2018/071740
§ 371 (c)(1),
(2) Date: Apr. 7, 2020

(87) PCT Pub. No.: WO2019/076510
PCT Pub. Date: Apr. 25, 2019

(65) Prior Publication Data
US 2020/0305738 A1    Oct. 1, 2020

(30) Foreign Application Priority Data

Oct. 19, 2017 (EP) .................... 17197341

(51) Int. Cl.
*A61B 5/024* (2006.01)
*A61B 5/00* (2006.01)
*A61B 5/361* (2021.01)

(52) U.S. Cl.
CPC ...... *A61B 5/02416* (2013.01); *A61B 5/02405* (2013.01); *A61B 5/361* (2021.01);
(Continued)

(58) Field of Classification Search
None
See application file for complete search history.

(56) References Cited

U.S. PATENT DOCUMENTS 9,907,474 B2    3/2018  Den Brinker et al.
2010/0268056 A1  10/2010  Picard et al.
(Continued)

FOREIGN PATENT DOCUMENTS

EP    2438849 A1 *  4/2012  ......... A61B 5/02416
JP    2016202347 A   12/2016
(Continued)

OTHER PUBLICATIONS

Lee et al., "Comparison Between Red, Green and Blue Light Reflection Photoplethysmography for Heart Rate Monitoring During Motion," 35th Annual International Conference of the IEEE EMBS, Jul. 3-7, 2013, pp. 1724-1727.
(Continued)

*Primary Examiner* — Jay B Shah
(74) *Attorney, Agent, or Firm* — Workman Nydegger

(57) ABSTRACT

A computer-implemented method for direct photoplethysmography or direct PPG comprises obtaining during a time interval plural PPG signals for respective sensors in a wearable device; and combining the plural PPG signals to thereby obtain a multi-sensor PPG signal.

18 Claims, 10 Drawing Sheets

(52) U.S. Cl.
CPC ............ *A61B 5/726* (2013.01); *A61B 5/7221* (2013.01); *A61B 5/7246* (2013.01); *A61B 5/7264* (2013.01); *A61B 5/7278* (2013.01)

(56) References Cited

U.S. PATENT DOCUMENTS

| | | |
|---|---|---|
| 2011/0077484 A1 | 3/2011 | Slyke et al. |
| 2013/0272393 A1 | 10/2013 | Kirenko et al. |
| 2015/0282724 A1 | 10/2015 | McDuff et al. |
| 2016/0220128 A1 | 8/2016 | Den Brinker et al. |
| 2017/0014040 A1 | 1/2017 | Shim et al. |
| 2017/0156593 A1* | 6/2017 | Ferber .................. A61B 5/0806 |
| 2017/0238805 A1 | 8/2017 | Addison et al. |

FOREIGN PATENT DOCUMENTS

| | | |
|---|---|---|
| JP | 2016538005 A | 12/2016 |
| WO | 2014024104 A1 | 2/2014 |
| WO | 2016207862 A1 | 12/2016 |

OTHER PUBLICATIONS

Kamshilin et al., "A New Look at the Essence of the Imaging Photoplethysmography," Scientific Reports, vol. 5, May 21, 2015, pp. 1-9.

Extended European Search Report and Written Opinion from EP Application No. EP17197341.5, dated Apr. 20, 2018.

International Search Report and Written Opinion from PCT Application No. PCT/EP2018/071740, dated Sep. 24, 2018.

Office Action from corresponding Japanese Application No. 2020-515754, dated May 17, 2022.

* cited by examiner

COMPUTER-IMPLEMENTED METHOD AND SYSTEM FOR DIRECT PHOTOPLETHYSMOGRAPHY (PPG) WITH MULTIPLE SENSORS

FIELD OF THE INVENTION

The present invention generally relates to photoplethysmography or PPG, an optical technique to detect blood volume changes that enables to monitor various physiological parameters. The invention more particularly concerns direct PPG or so-called contact PPG wherein the measurement components, i.e. light sources and photodetectors, are in direct contact with the skin of the monitored person. The invention generally envisages to improve the signal quality in direct PPG when multiple sensors are available.

BACKGROUND OF THE INVENTION

Photoplethysmography or PPG is an optical technique that allows to monitor one or more physiological parameters by detecting blood volume changes in peripheral circulation. PPG makes use of light absorption by blood to track these volumetric changes. When a light source illuminates the skin, the reflected light varies as blood flows. A light sensor then converts these variations in light reflection into a digital signal, the so-called PPG signal. PPG signals are typically recorded using a pulse oximeter or photodetectors, for instance the camera integrated in an electronic device like a person's smartphone or other smart wearable or non-wearable device.

PPG can be used, among other applications, to monitor cardiovascular and hemodynamic parameters such as heartrate, heartrate variability, blood pressure, or to monitor other physiological variables such as stress, respiration or autonomic functions. One key part of an accurate monitoring with PPG is to obtain a high-quality, artefact-free signal, as PPG can be affected by various sources of noise.

International patent application WO 2014/024104, entitled "Device and Method for Extracting Physiological Information" and filed by Koninklijke Philips N. V., describes a method to improve the accuracy of remote PPG or non-contact-PPG, which is typically used to track a larger region of interest (e.g. a face) in daily applications like fitness. The method divides the region of interest in spatial sub-regions and partitions the PPG signal in signal subsets representing the respective sub-regions. The signal subsets are processed separately. The processing may involve a quality estimation. Thereafter, the signal subsets are combined into an enhanced signal. Distorted sub-signals can be attenuated or eliminated from the combined signal.

Also United States Patent Application US 2013/0272393 A1, entitled "Video Coding and Decoding Devices and Methods Preserving PPG Relevant Information" and filed by Koninklijke Philips N. V., concerns remote PPG.

Although remote PPG is non-obtrusive for the monitored person, it poses major challenges to signal detection and signal processing. As a consequence, the use of remote PPG remains limited to everyday applications like leisure or fitness as its accuracy and reliability are insufficient for medical applications.

As opposed to remote PPG, the present invention concerns direct PPG or contact PPG, wherein the measurement components are in direct contact with the skin in order to obtain a more reliable, more accurate PPG signal that facilitates medical diagnosis.

In applications where a direct PPG signal is processed to determine the heartrate variability, inaccuracies can result from a low signal quality. While a partially good quality signal gives sufficient information to make a reliable analysis, the presence of artefacts can severely affect the quality and can lead to misleading results. Consequently, there is a need to have a direct PPG signal as clean as possible, and to identify and remove bad quality portions to keep only the good quality ones for further analysis.

Artefacts include motion, bad positioning of the skin with respect to the light sensor or ambient light interference. The article "A new look at the essence of the imaging photoplethysmography" from the authors Alexei A. Kamshilin et al. also reports another artifact frequently observed in PPG signals: PPG waveform inversion. This phenomenon is manifested by a signal, or a part of the signal, being inverted in comparison with the usual orientation of the signal. This phenomenon has been observed in adjacent areas of the skin, one area presenting a signal in the usual orientation and the adjacent area presenting a signal in the opposite orientation. This leads to a quality loss of the PPG signal when these two areas are used to extract the signal. Explanations for this phenomenon are still to be validated.

In order to improve the quality of direct PPG signals recorded by means of a camera, it has been suggested to divide the image pixels into a matrix of sub-regions, or quadrants, and to apply a selection algorithm that determines the optimal sub-image, i.e. the quadrant whose PPG signal has the best quality, called the optimal region of interest.

The article "Investigation of Five Algorithms for Selection of the Optimal Region of Interest in Smartphone Photoplethysmography" from authors Rong-Chao Peng et al. describes five algorithms to select the optimal region of interest:

the Variance (VAR) algorithm selects the quadrant whose PPG waveform has the highest variance, i.e. the highest signal power, as optimal region of interest;

the Spectral Energy Ratio (SER) algorithm selects the quadrant whose PPG signal has the highest spectral energy ratio, i.e. which indicates the highest proportion for cardiac activity, as optimal region of interest;

the Template Matching (TM) algorithm selects the quadrant whose PPG signal has the highest similarity with a template waveform as optimal region of interest;

the Temporal Difference (TD) algorithm selects the quadrant whose PPG signal has the highest average intensity variation for pixels between adjacent frames as the optimal region of interest; and the Gradient (GRAD) algorithm selects the quadrant whose PPG signal has the greatest average light intensity gradient as the optimal region of interest.

The article of Peng et al. concludes that the TM and TD algorithms outperform the others in selecting the optimal region of interest and consequently in selecting the PPG signal that enables to estimate physiological parameters with improved accuracy.

The article "Detection of the Optimal Region of Interest for Camera Oximetry" from authors Walter Karlen et al. describes yet another algorithm to determine the preferred quadrant or optimal region of interest. The proposed algorithm considers only blue channels and extracts beats or pulses from the PPG signal through mean pixel intensity calculation and the incremental-merge segmentation (IMS) algorithm. In other words, the selected optimal region of interest has the PPG signal with the highest pulses. Karlen et al. further also teach to select the incandescent white balance mode as preferable setting for PPG on the Samsung Galaxy Ace mobile phone.

In addition to selecting a subset of pixels, the so called optimal region of interest, it has been suggested to generate a PPG signal by choosing a specific color channel. The article "Comparison between red, green and blue light reflection photoplethysmography for heart rate monitoring . . . " from Jihyoung Lee et al. for instance suggests that green light is more suitable for monitoring heartrate.

United States Patent Application US 2011/0077484 A1, entitled "Systems and Methods for Identifying Non-Corrupted Signal Segments for Use in Determining Physiological Parameters" and filed by Assignee Nellcor Puritan Bennett Ireland, teaches to analyse the quality of direct PPG signal segments by processing the wavelet transform of PPG signals with a trained neural network. This results in corrupted and non-corrupted PPG signal segments being identified. Corrupted signal segments are removed or replaced by earlier received, non-corrupted PPG signal segments.

The known solutions rely on the selection of a single region of interest and extract the PPG signal from this selected region of interest. The selected region of interest is static, i.e. the optimal region is a single sub-region of pixels that is considered to be the same for the whole measurement. This can lead to unsatisfying results when the optimal sub-region to extract the PPG signal varies across the measurement. The extracted PPG signal may then contain inversions and/or bad quality sections that reduce the accuracy of physiological parameter estimation, e.g. the accuracy of heart rate variability, and consequently the accuracy of any disease diagnosis, for instance AF diagnosis, built thereon.

Likewise, the color selection in known systems for direct PPG signal extraction is made beforehand and the same color is statically used for every analysis.

In the development of wearables such as smart phones, smart watches, etc., there is a tendency to integrate plural sensors. Recent wearables for instance are announced to have plural photodetectors placed in a raster. In line with the existing solutions for PPG that statically select an optimal color and/or statically select an optimal region of interest, the availability of plural sensors may give rise to PPG implementations with static selection of an optimal sensor: some quality measure may be applied to the different sensors, and a single sensor may be selected for PPG signal extraction.

United States Patent Application US 2010/0268056A1, entitled "Washable Wearable Biosensor" and filed by Massachusetts Institute of Technology, describes a wearable with multiple sensors. Paragraphs [0016] and [0076] of US2010/0268056A1 specify that in certain embodiments, multiple PPG signals that are obtained by multiple PPG sensors are combined using signal processing to reduce noise caused by motion artefacts. US 2010/0268056A1 however remains silent on how the multiple PPG signals should be combined.

Furthermore, none of the prior art solutions aims at improving signal quality target the camera settings that may negatively influence the direct PPG signal quality across various vendors and types of smart devices.

It is therefore an objective of the present invention to disclose a computer-implemented method for direct PPG that resolves one or more of the above-identified shortcomings of existing solutions. More particularly, it is an objective to disclose a method for direct PPG when multiple sensors are available with improved accuracy and reliability.

SUMMARY OF THE INVENTION

According to the present invention, the above identified objective is realised by the computer-implemented method for direct photoplethysmography or direct PPG as defined by claim 1, comprising:
  obtaining during a time interval plural PPG signals for respective sensors in a wearable device; and
  combining the plural PPG signals to thereby obtain a multi-sensor PPG signal, wherein the method comprises:
  processing each PPG signal of the plural PPG signals to identify good quality segments of the PPG signal wherein a quality measure of the PPG signal is above a threshold and bad quality segments of the PPG signal wherein the quality measure of the PPG signal is below the threshold;
  removing the bad quality segments from each PPG signal of the plural PPG signals; and
  combining temporal corresponding good quality segments of the plural PPG signals to obtain the multi-sensor PPG signal.

Thus, multiple direct PPG signals that are obtained from multiple sensors, e.g. a plurality of photodiodes integrated in a single wearable device or a plurality of LEDs surrounding a single photodiode and switched on sequentially such that different colors are measured through a single photodiode, are combined into a multi-sensor PPG signal. Thanks to the combining of PPG signals of multiple sensors, good quality PPG information is not eliminated through static upfront selection of a single sensor. Good quality portions of the different PPG signals will be present in the multi-sensor PPG signal, hence increasing the presence of valuable information in the multi-sensor PPG signal, as well as the accuracy and reliability of any physiological parameter estimation derived therefrom.

The PPG signals obtained from multiple sensors are combined based on a quality assessment. PPG signals are obtained for plural sensors of a wearable device. Each of these PPG signals is segmented into time segments with a typical length ranging from a few seconds up to the entire measurement interval. If PPG signals are obtained for a time interval of 60 seconds, these PPG signals may for instance be segmented into twelve time segments of 5 seconds each. The segmentation is identical for all PPG signals such that for each segment in a PPG signal, temporally corresponding segments exist in the PPG signals obtained for other sensors. Each PPG signal segment is then subjected to a quality assessment. According to some quality measure, a distinction is made between good quality PPG signal segments and bad quality PPG signal segments, i.e. PPG signal segments for which the quality assessment exceeds a given quality threshold and PPG signal segments for which the quality assessment stays below the given threshold. The bad quality PPG signal segments are eliminated, i.e. they are removed from the respective PPG signals. The good quality segments of the different PPG signals that temporally correspond with each other are combined: such segments are for instance added, or a weighted sum of such segments is made wherein the weights are proportional to the respective quality value determined for such segments, or alternative combinations may be considered as will be appreciated by the person skilled in the art. As a result, a multi-sensor PPG signal is composed that performs better in terms of accuracy and reliability because it combines only the good quality portions of the PPG signals and leaves bad quality portions of the PPG signals out of the multi-sensor PPG signal.

It is noticed that each PPG signal in the method according to the present invention represents a direct PPG signal or contact PPG signal obtained for a different sensor out of a plurality of sensors integrated in a single wearable and placed for instance in a raster. The sensors preferably are of the same type, e.g. all of them are photodetectors, such that the PPG signals are easily combinable, e.g. by summing together or averaging the PPG signals.

It is further noticed that the time interval in the method according to the present invention corresponds to a time interval during which a continuous direct PPG measurement is carried out. The time interval shall typically range from a few tens of seconds, e.g. 30 seconds, up to a few minutes, e.g. 3 minutes. Thus, the time interval may for instance correspond to the length of a video frame of 60 seconds if an AF patient is requested to make a 1-minute PPG measurement twice a day with his wearable having plural cameras or it may correspond to a measurement interval of 1 or several minutes if plural photodiodes or plural LEDs surrounding a photodiode are used to obtain the PPG signals for monitoring purposes.

In line with the present invention, the PPG signals obtained during such time interval from different sensors may be combined statically into the multi-sensor PPG signal or they may be combined dynamically into the multi-sensor PPG signal. Statically combining PPG signals of multiple sensors implies that the PPG signals are combined in the same manner throughout a measurement time interval. Statically combining the PPG signals of multiple sensors may for instance be obtained by averaging the PPG signals of good quality, or by adding or averaging PPG signals of good quality of a particular subset of sensors. When statically combining the PPG signals, the PPG signals may be combined in a different manner in subsequent time intervals. As an example, static multi-sensor PPG may involve making an assessment and depending on that assessment adding PPG signals of a first subset of sensors in a first time interval, e.g. the PPG signals obtained from photodiodes A and B, whereas PPG signals of a second subset of sensors, different from the first subset, e.g. PPG signals of photodiodes A, C and D, are added in a second time interval based on a new assessment that was made for the second time interval, herewith anticipating inter-measurement differences resulting for instance from a different positioning of the wearable device on the person's skin. Dynamically combining the PPG signals is realized by combining PPG signals of different subsets of sensors in different temporal sub-segments of the time interval, to anticipate intra-measurement differences, as will be explained further below.

It is further noticed that within a time interval, PPG signals obtained for different colors may be selected or combined, and the colors that are selected or combined may vary between the sensors, as will be further explained below.

It is further also noticed that for a single sensor, one or more spatial sub-region may be selected or combined. The spatial sub-regions that are selected or combined may also vary between the sensors, as will be explained further below.

In embodiments of the computer-implemented method for direct PPG according to the present invention, as defined by claim 2, the good quality segments comprise non-inverted segments and inverted segments, and the processing of each PPG signal further comprises identifying the inverted segments and reverting the inverted segments.

Indeed, inverted PPG signals can be maintained as good quality PPG signals after being reversed. In advantageous embodiments of the method according to the invention, the quality assessment distinguishes between good quality non-inverted PPG signal segments, inverted PPG signal segments and bad quality PPG signal segments. This may for instance be achieved by inverting each of the PPG signal segments, applying the quality measure and verifying if the quality measure exceeds the given threshold. If this is the case, the PPG signal segment is an inverted PPG signal segment that can be maintained for the multi-sensor PPG signal composition on the condition it is reverted to become a non-inverted, good quality PPG signal. Reverting the PPG signal segment boils down to changing the sign of the samples. By reverting inverted PPG signal segments and maintaining such PPG signal segments for the composition of the multi-sensor PPG signal, the accuracy and reliability of the latter multi-sensor PPG signal is further enhanced.

In further embodiments of the computer-implemented method for direct PPG according to the present invention, as defined by claim 3, the processing of each PPG signal comprises:
  wavelet transforming the PPG signal to obtain a wavelet transformed PPG signal; and
  supplying the wavelet transformed PPG signal to a neural network trained to identify good quality segments of the PPG signal and bad quality segments of the PPG signal.

Thus, preferred embodiments of the invention wavelet transform the PPG signal segments. The wavelet transformed PPG signal segments are then supplied to a neural network that has been trained with sample sets to distinguish good quality signal segments and bad quality signal segments. The skilled person however will appreciate that alternative quality measures exist to distinguish good quality PPG signal portions from bad quality PPG signal portions that do not rely on wavelet transformation and/or neural networks.

In further embodiments of the computer-implemented method for direct PPG according to the invention, as defined by claim 4, the neural network is further trained to identify the inverted segments.

Indeed, the neural network is preferably also trained to distinguish inverted PPG signal segments. These inverted PPG signal segments may then be reverted to become good quality PPG signal segments retained for the multi-sensor PPG signal composition.

Embodiments of the computer-implemented method for direct PPG according to the present invention, as defined by claim 5, comprise:
  generating plural multi-sensor PPG signals similar to the multi-sensor PPG signal for respective colors from a color space.

Indeed, optionally, the PPG signals are obtained for different colors of a color space, for instance red, green and blue in the RGB space or cyan, yellow, and magenta in the CYMK space. The PPG signals obtained from plural sensors for a single color, e.g. green, may then be combined into a multi-sensor PPG signal for that color. This way, multi-sensor PPG signals can be generated for the respective colors of the color space. The multi-sensor PPG signal of the color with highest quality may then be selected statically or dynamically as will be explained below.

Embodiments of the computer-implemented method for direct PPG according to the present invention, as defined by claim 6, further comprise:

determining a quality measure for each one of the colors; and selecting amongst the plural multi-sensor PPG signals the multi-sensor PPG signal for the color with highest quality measure.

Thus, advantageous embodiments of the invention produce multi-sensor PPG signals for plural colors of a color space, and statically select a single multi-sensor PPG signal of a single color based on a quality assessment. The selected multi-sensor PPG signal of a single color is then used for physiological parameter estimation. For the next time interval, it is however possible that the multi-sensor PPG signal of a different color is selected.

Alternative embodiments of the computer-implemented method for direct PPG according to the present invention, as defined by claim 7, further comprise:

determining a quality measure for each one of the colors; and combining multi-sensor PPG signals for plural colors into a multi-color multi-sensor PPG signal.

Indeed, as an alternative to selecting a single color, the multi-sensor PPG signals of different colors may be combined provided that the phase-shift that is existing between PPG signals obtained for different colors, is compensated for.

Embodiments of the computer-implemented method for direct PPG according to the invention, as defined by claim 8, further comprise:

obtaining during the time interval plural PPG signals for respective colors and respective sensors;

processing each PPG signal of the plural PPG signals to identify good quality segments of the PPG signal wherein a quality measure of said PPG signal is above a threshold and bad quality segments of the PPG signal wherein the quality measure of the PPG signal is below the threshold;

removing the bad quality segments from each PPG signal of the plural PPG signals; and combining temporal corresponding good quality segments of the plural PPG signals to obtain the multi-color multi-sensor PPG signal.

Hence, advanced embodiments of the invention segment each PPG signal into time segments with a typical length of a few seconds, e.g. 5 seconds. This is done for each color. The individual PPG signal segments are processed to assess the quality thereof. They may for instance be wavelet transformed and fed into a neural network that distinguishes good quality segments, bad quality segments and possibly inverted segments. Bad quality segments are eliminated, and good quality segments that temporally correspond are combined across the sensors and across the colors in order to dynamically generate a multi-color multi-sensor PPG signal wherein each segment may be composed of different colors and different sensors. The so-obtained multi-color multi-sensor PPG signal is optimal in terms of accuracy and reliability as it dynamically combines the best of colors with the best of sensors while eliminating all PPG signal portions of poor quality.

Embodiments of the computer-implemented method for direct PPG according to the invention, as defined by claim 9, further comprise:

obtaining during the time interval for at least one of said sensors plural PPG signals for respective sub-regions of said sensor, each sub-region of said sub-regions covering multiple pixels; and combining the plural PPG signals to thereby obtain a multi-sensor multi-region PPG signal or a multi-color multi-sensor multi-region PPG signal.

Thus, in advanced embodiments of the invention, a single sensor may be further subdivided in sub-regions. As an example, the lens of a camera may be subdivided in four quadrants. The pixels of each sub-region may be used to produce a sub-region PPG signal. Thus, plural PPG signals are obtained for a single sensor. It is even possible that plural sub-region PPG signals are obtained for respective colors of a color space. The sub-region PPG signals may be combined statically or dynamically into a multi-region PPG signal, i.e. a single artificial PPG signal for the respective sensor composed of sub-regions and/or colors, and that multi-region PPG signal may be combined with the PPG signals of other sensors in order to obtain the multi-sensor PPG signal according to the present invention. Alternatively, the sub-region PPG signals of a sensor may be combined directly with the PPG signals of other sensors to compose a multi-sensor multi-region PPG signal, or even a multi-color multi-sensor multi-region signal. In any of the above described scenario's, the individual sub-region PPG signals may first be processed in order to remove bad quality segments thereof and to revert inverted segments thereof. The so-obtained multi-sensor multi-region PPG signal or the so obtained multi-color multi-sensor multi-region PPG signal is optimal in terms of accuracy and reliability as it combines the best of sub-regions and the best of colors for plural sensors in a wearable device.

Embodiments of the computer-implemented method for direct PPG according to the present invention, as defined by claim 10, further comprise locking settings of one or more of the sensors during the time interval, the settings at least comprising:

diaphragm;

sensor setting for light sensitivity; and light exposure time.

Indeed, in order to reduce the amplitude noise and consequently improve the accuracy and reliability of the PPG signals, the sensor settings are preferably locked during the full measurement time interval in case one or more of the sensors are cameras. The camera settings that are preferably locked at least must include the diaphragm, the light sensitivity or sensitivity of the sensor chip, and the light exposure time or duration of how long the sensor is exposed to light. Other camera settings may however also be locked during the complete PPG measurement time interval in order to further reduce noise and further improve the accuracy of PPG measurements. It is noticed that locking the camera settings brings advantages in noise reduction and accuracy independent from the multi-sensor PPG signal composition. Thus, also in situations where no plural PPG signals are combined to compose a multi-sensor PPG signal and/or in situations where no plural colors are combined to compose a multi-color PPG signal and/or in situations where no plural sub-regions are combined to compose a multi-region PPG signal, the locking of camera settings during PPG signal acquirement brings substantial advantages in amplitude noise reduction. In case other sensors are used, e.g. photodiodes, it is possible that certain settings preferably vary during the measurement time interval because such photodiodes, as opposed to cameras, are more suited to obtain PPG signals.

Embodiments of the computer-implemented method for direct PPG according to the present invention, as defined by claim 11, further comprise detecting peaks in the multi-sensor PPG signal, and thereto:

detecting initial peaks in the multi-sensor PPG signal;
windowing the initial peaks in the multi-sensor PPG signal to thereby generate windowed initial peaks;
averaging the windowed initial peaks in the multi-sensor PPG signal to thereby generate a peak template;
correlating the initial peaks with the peak template;
maintaining initial peaks for which a correlation measure exceeds a correlation threshold as peaks; and
dropping initial peaks for which the correlation measure does not exceed the correlation threshold.

Thus, preferred embodiments of the present invention apply a template matching peak detection algorithm to detect peaks in the composed multi-sensor PPG signal. In a first step, initial amplitude peaks are detected in the multi-sensor PPG signal. Each initial peak is windowed through a window that filters a limited set of samples preceding the detected initial peak and a limited set of samples following the initial peak out of the multi-sensor PPG signal. The so-obtained windowed initial peaks are then averaged to compose a peak template that corresponds to the average initial peak. Each one of the detected initial peaks is thereafter compared or correlated with the template peak and initial peaks whose correlation with the template peak stays below a predetermined threshold are eliminated, i.e. they are no longer considered to constitute peaks. The template matching peak detection algorithm may be repeated iteratively, possibly with increasing correlation threshold, until all peaks satisfy a final, desired correlation threshold. The final set of peaks may then be used for physiological parameter estimation.

Embodiments of the computer-implemented method for direct PPG according to the present invention, defined by claim 12, further comprise:
extracting an RR-tachogram by determining a time difference between subsequent peaks in the multi-sensor PPG signal.

Thus, embodiments of the invention suitable for applications wherein the heartbeat or heartrate is monitored or analysed further may extract an RR-tachogram from the peaks determined in the multi-sensor PPG signal. The timing of the maintained peaks thereto is considered. The time difference between each two subsequent peaks is determined to compose the RR-tachogram.

Embodiments of the computer-implemented method for direct PPG according to the invention, defined by claim 13, further comprise:
processing the multi-sensor PPG signal to identify good quality segments of the multi-sensor PPG signal wherein a quality measure of the multi-sensor PPG signal is above a threshold and bad quality segments of the multi-sensor PPG signal wherein the quality measure of the multi-sensor PPG signal is below said threshold;
removing peaks within the bad quality segments from the multi-sensor PPG signal before extracting the RR-tachogram; and
removing from the RR-tachogram the RR-tachogram intervals located totally or partially within the bad quality segments of the multi-sensor PPG signal.

Thus, the RR-tachogram may be processed to contain exclusively the RR-tachogram intervals that lie within good quality intervals of the multi-sensor PPG signal. Thereto, the quality of segments of the multi-sensor PPG signal must be assessed according to a measure to distinguish good quality segments from bad quality segments in the multi-sensor PPG signal. The quality assessment may be identical or similar to the quality assessment used for the individual PPG signals, for instance based on wavelet transforming and neural network analysis, but alternative quality measures may be applied as well, as will be appreciated by the person skilled in the art. The quality assessment results in an identification of good quality segments and bad quality segments in the multi-sensor PPG signal that is thereafter used to eliminate peaks that passed the peak detection algorithm but which are located in a bad quality segment of the multi-sensor PPG signal from this multi-sensor PPG signal. Consequently, also the RR-tachogram intervals that are located entirely or partially within such bad quality intervals of the multi-sensor PPG signal are removed from the RR-tachogram to obtain an RR-tachogram with improved reliability.

Embodiments of the computer-implemented method for direct PPG according to the present invention, as defined by claim 14, further comprise:
determining a variability in the time difference between subsequent peaks; and
determining from the variability an atrial fibrillation risk score.

Embodiments of the invention suitable for atrial fibrillation (AF) risk analysis further determine the variability in the time difference between subsequent peaks maintained by the peak detection algorithm, i.e. the heartbeat variability or heartrate variability. An AF score is determined proportional to this variability and when this AF score exceeds a predefined threshold the patient or monitored person may be warned such that a clinician can be consulted for further diagnosis.

In addition to a computer-implemented method as defined by claims 1-14, the present invention also concerns a corresponding computer program product as defined by claim 15, comprising computer-executable instructions for performing the method when the program is run on a computer.

The present invention further also concerns a computer readable storage medium as defined by claim 16, comprising the computer program product.

The present invention further also concerns a data processing system as defined by claim 17, programmed for carrying out the method according to one of claims 1-14.

DETAILED DESCRIPTION OF EMBODIMENT(S)

Figure 1:
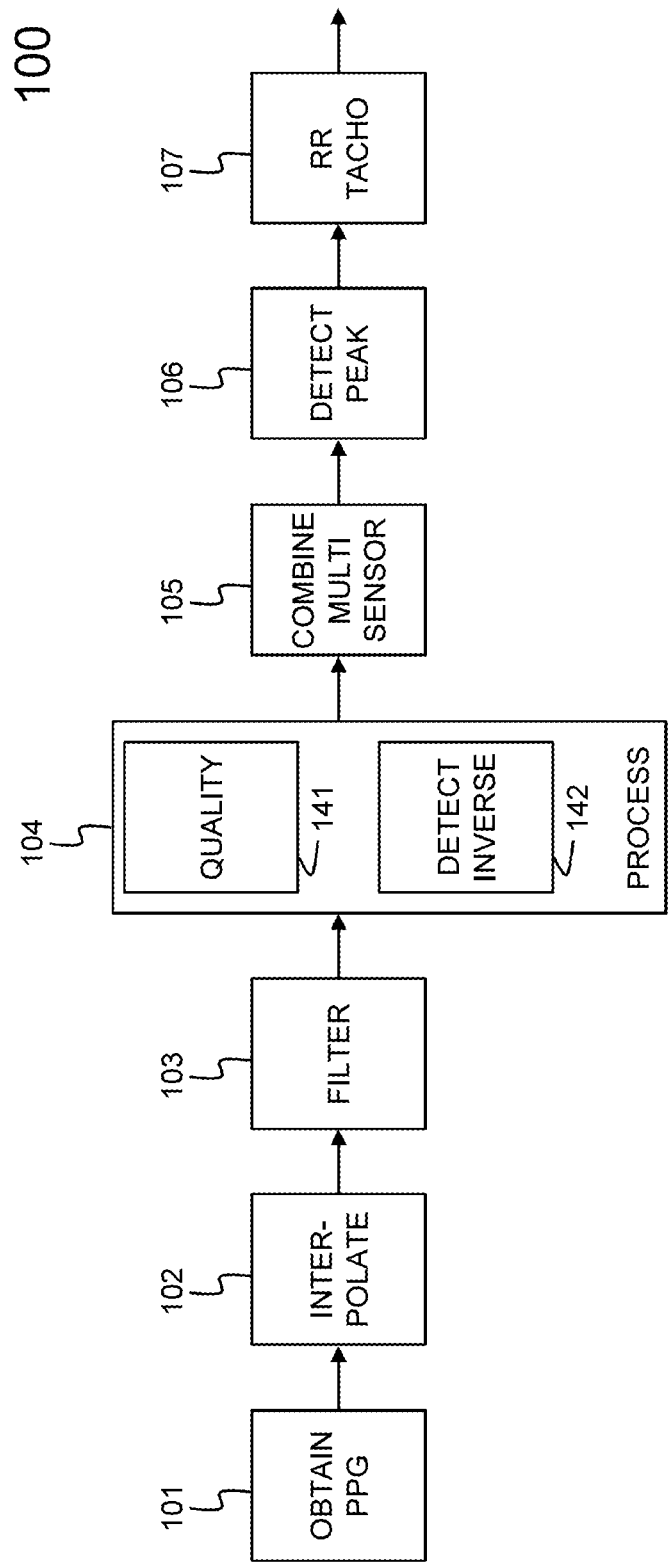
FIG. 1 is a block scheme illustrating an embodiment of the computer-implemented method for direct PPG according to the present invention.

FIG. 1 shows the steps subsequently executed in an embodiment 100 of the method for direct PPG according to the present invention. In a first step 101, plural PPG signals are obtained from respective sensors in a wearable device, for instance plural photodiodes integrated in a raster in a smartwatch. The PPG signals are obtained for a single color, or alternatively PPG signals may be obtained for plural colors, e.g. R, G and B colors or C, M and Y colors for each of the sensors. The PPG signals may be obtained for the entire surface of a sensor or PPG signals may be obtained for sub-regions of a sensor, i.e. subsets of neighbouring pixels like for instance quadrants of a lens in case a sensor would be a camera. The PPG signals are obtained during a pre-defined time interval that typically is set from a few tens of seconds up to a few minutes. The PPG signals are obtained at an exemplary frequency of 30 Hz, meaning that 30 images per second are taken by the imaging device to serve as basis for the PPG signals. Tests have demonstrated that it is of importance that certain settings of sensors, e.g. a camera or imaging device, are locked during the time interval wherein the PPG signals are obtained, because locking the sensor settings substantially improves the quality of the PPG signals. These settings at least comprise the diaphragm and the light sensitivity or light exposure. As the PPG signals are obtained by a wearable device, e.g. sensors integrated in a smartphone, it is advised to remotely control the sensor settings to stay locked during the execution of step 101.

In a second step 102, interpolation is performed for each signal to ensure an equal sampling of all signals. Thereafter, in step 103, each PPG signal is filtered, typically bandpass filtered to remove noise and obtain PPG signals within the frequency band of interest. The frequency band of interest may be determined by the medical application. In case of heartbeat, heartrate or heartrate variation analysis, the frequency band of interest for instance is a frequency band ranging from 30 Hz to 200 Hz. It is noticed that the step 101 of obtaining PPG signals, the interpolation step 102 and the filtering step may jointly form part of pre-processing that is executed remotely, e.g. on the smartphone or other electronic device worn by the person whereon direct PPG is applied. Subsequent steps 104-107 that will be explained in the following paragraphs but generally are more processing intensive, shall typically be executed centrally, i.e. on a server with higher processing capacity, although it is not excluded that certain steps or sub-steps in future embodiments of the invention also may be executed remotely on electronic devices since processing power of such electronic devices continues to grow.

In step 104, each PPG signal is processed. The processing involves both assessing the quality in sub-step 141 and detecting inversion in sub-step 142. Assessing the quality and detecting inversion may be applied for the entire PPG signal over the entire time interval in static implementations of the invention. Alternatively, the quality assessment and inversion detection is applied on time segments of the PPG signal in dynamic implementations of the invention. As a result, good quality portions and bad quality portions are identified in the PPG signal. Portions of the PPG signal that are inverted, are reverted to become good quality portions that remain useful. Bad quality portions shall be removed from the PPG signal.

In step 105, plural PPG signals obtained from different sensors that form part of a single wearable device are combined into a multi-sensor PPG signal, i.e. an artificially composed PPG signal that contains information extracted from plural PPG signals representing plural sensors. Obviously, the good quality portions of plural PPG signals are combined into a single multi-sensor PPG signal that performs better in terms of accuracy and reliability for subsequent physiological parameter extraction. In static implementations of the invention, entire PPG signals of different sensors found to have good quality, either of a single color or of multiple synchronized colors, are combined into a single multi-sensor PPG signal. In dynamic implementations of the invention, temporally corresponding segments of plural PPG signals are combined. The set of PPG signal segments that is combined typically varies from time segment to time segment, i.e. different sensors and/or different colors may be represented in different time segments of the multi-sensor PPG signal because the quality of the different colors and the quality of the different sensors varies in time.

To the so composed multi-sensor PPG signal, a peak detection algorithm is applied in step 106 in order to detect peaks, and the inter-peak distance is determined in step 107 in order to extract an RR-tachogram, useful in analysis of the heartrate variability and AF risk level of a patient. Obviously, steps 106 and 107 may not be executed in embodiments of the invention that implement direct PPG for other purposes than heartbeat, heartrate or heartrate variability analysis.

Figure 2:
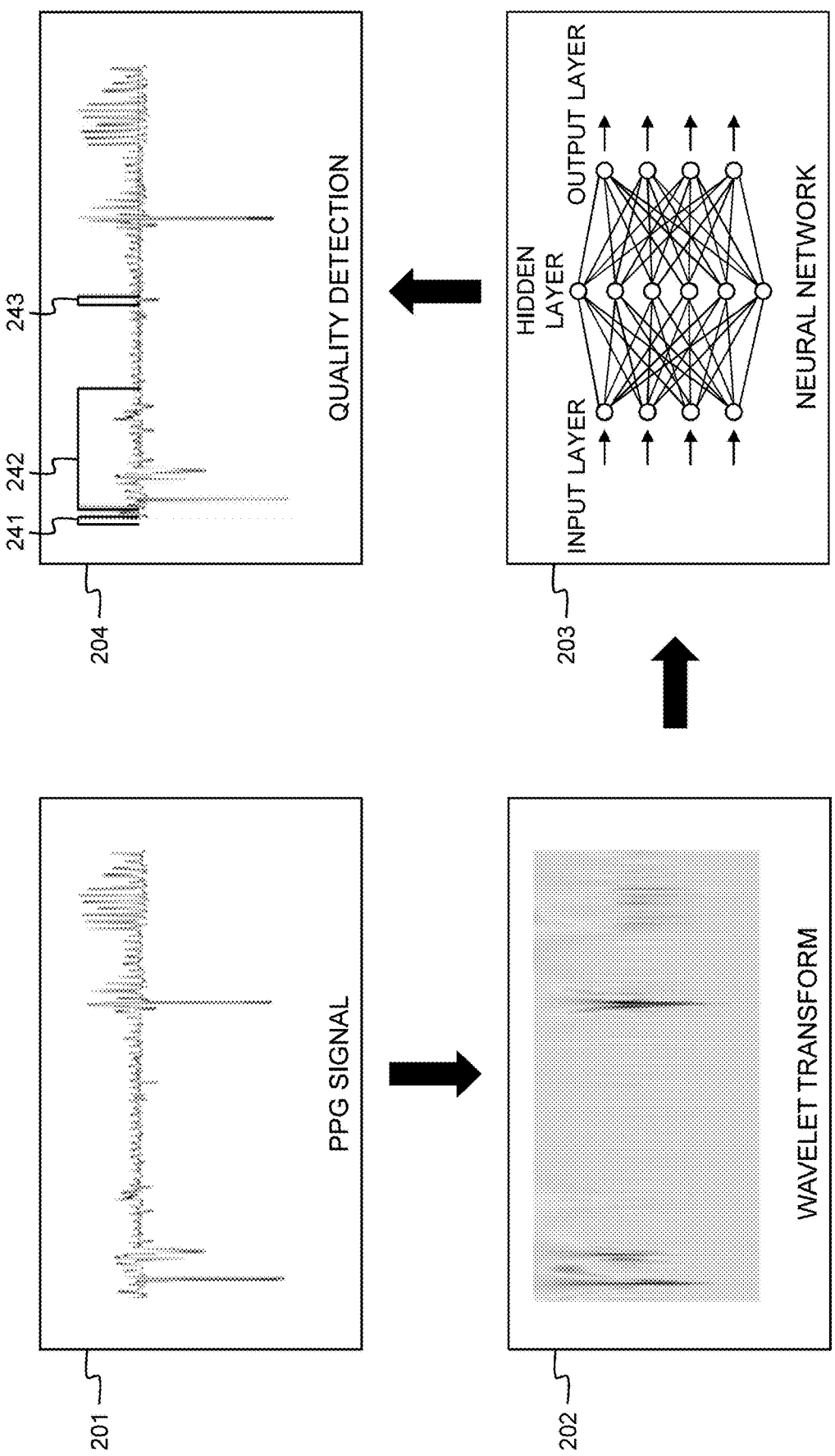
FIG. 2 illustrates the step of processing a PPG signal for quality assessment in embodiments of the computer-implemented method for direct PPG according to the present invention.

FIG. 2 illustrates the operation of step 104 in FIG. 1, i.e. the quality assessment and inversion detection, as executed in embodiments of the invention. Each PPG signal 201 is wavelet transformed thus resulting in the wavelet transformed PPG signal 202. This wavelet transformed PPG signal 202 is then fed into a neural network 203 that has been trained with sets of training data to distinguish good quality PPG signals, bad quality PPG signals, and inverted PPG signals. The outcome of the neural network 203 is that the PPG signal is either qualified as good quality PPG signal, bad quality PPG signal, or inverted PPG signal. In the latter case, the PPG signal is reverted and the reverted PPG signal is qualified as good quality PPG signal. In dynamic implementations of the present invention, the quality assessment based on wavelet transformation and neural network analysis is performed for each time segment of each PPG signal. As a result thereof, good quality portions are identified in the PPG signal 201 and bad quality portions 241, 242, 243 are identified in the PPG signal 201. The bad quality portions 241, 242, 243 at last are removed from the PPG signal 204. Likewise, in implementations of the invention wherein multiple colors are considered, the quality assessment and inversion detection described here above with reference to FIG. 2 may be applied to a single color if an upfront selection is made of a single color for instance as a result of a different quality assessment used for selecting the best color, may be applied for the entire PPG signals of plural colors in order to be able to statically combine good quality colors into a multi-color multi-region PPG signal, or may be applied to time segments of plural colors in order to be able to dynamically combine sensors and colors into a multi-color multi-sensor PPG signal.

Figure 3:
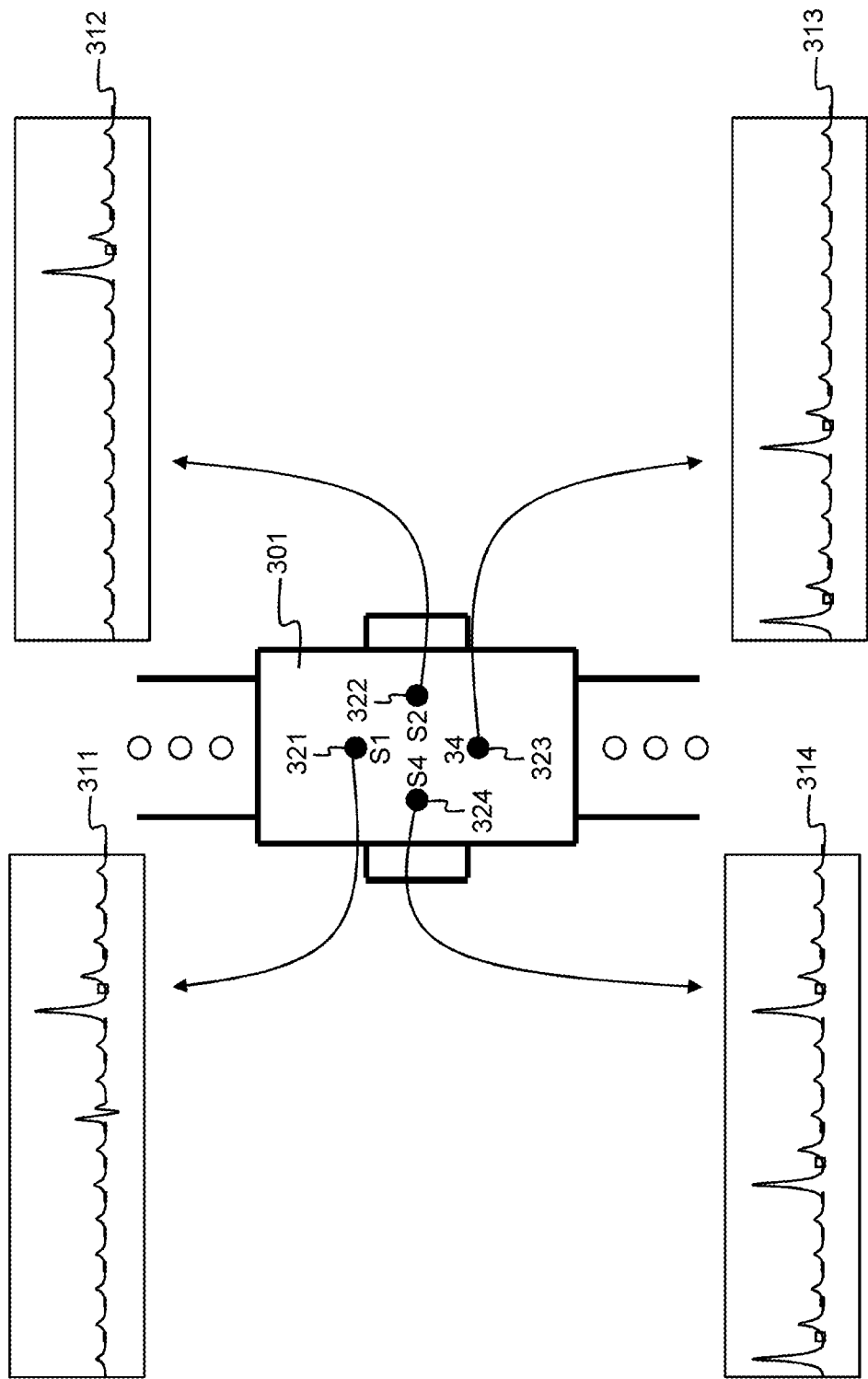
FIG. 3 illustrates the step of obtaining plural PPG signals for plural sensors in embodiments of the computer-implemented method for direct PPG according to the present invention.

FIG. 3 illustrates in more detail step 101 of obtaining plural PPG signals 311, 312, 313 and 314, from different sensors S1 or 321, S2 or 322, S3 or 323 and S4 or 324 integrated in a wearable device 301. In FIG. 3, four photodiodes are placed in a raster in a smartwatch 301: S1 or 321, S2 or 322, S3 or 323 and S4 or 324. The first photodiode, S1 or 321, is used to obtain a first PPG signal 311. The second photodiode, S2 or 322, is used to obtain a second PPG signal 312. The third photodiode, S3 or 323, is used to obtain a third PPG signal 313. The fourth photodiode, S4 or 324, is used to obtain a fourth PPG signal 314. The obtained PPG signals 311, 312, 313 and 314 differ because they result from light reflections in different parts of the body, and because of various artefacts like inversions. In line with the present invention, the PPG signals 311, 312, 313 and 314 obtained from different sensors will be combined into a single multi-sensor PPG signal with improved reliability and accurateness over the individual PPG signals 311, 312, 313 and 314. With reference to FIG. 4, FIG. 5, FIG. 6 and FIG. 7, the following paragraphs will describe different ways of combining the PPG signals obtained from plural sensors into a multi-sensor PPG signal.

Figure 4:
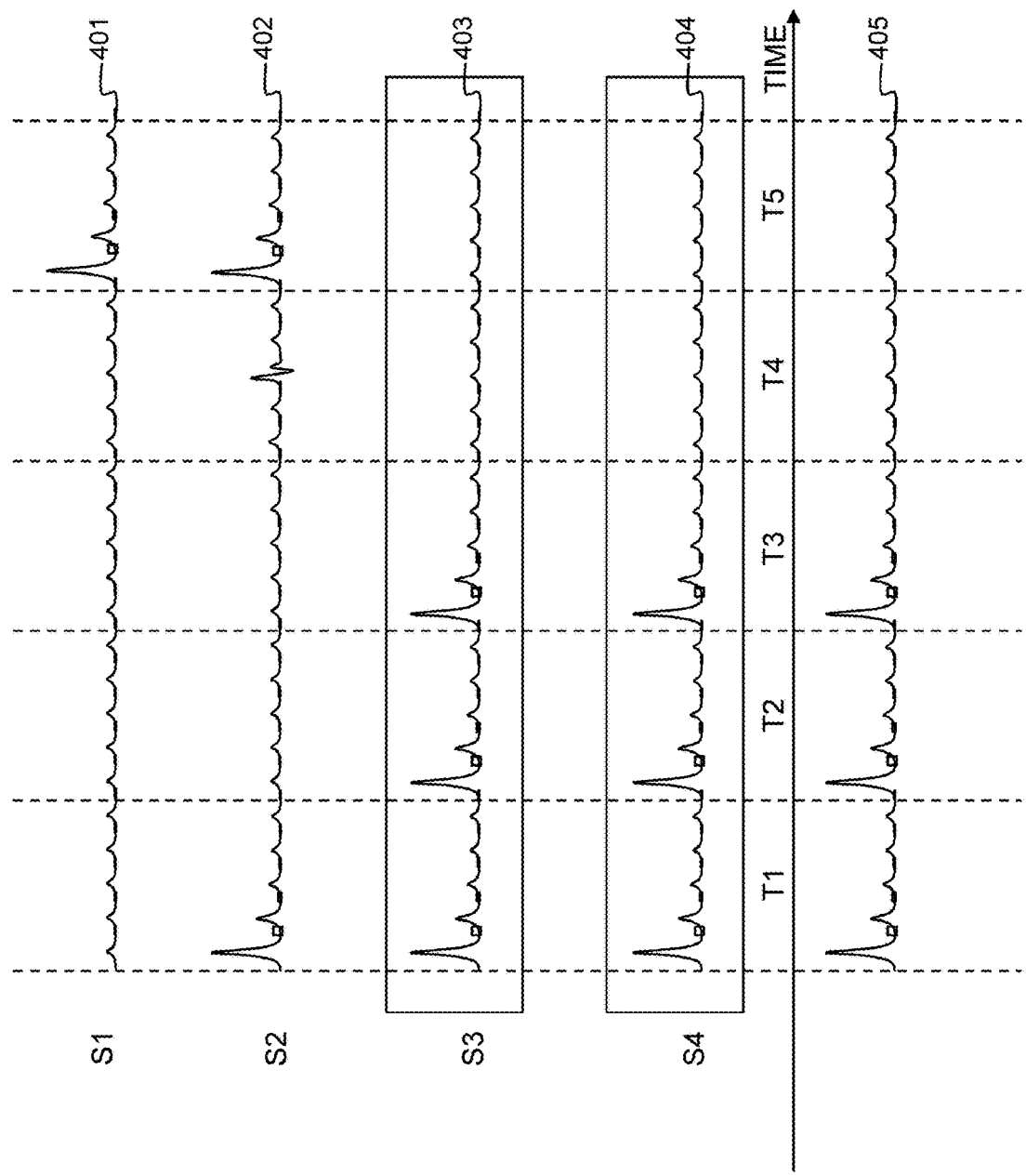
FIG. 4 illustrates the step of combining plural PPG signals into a multi-sensor PPG signal in embodiments of the computer-implemented method for direct PPG according to the present invention that implement static multi-sensor PPG.

FIG. 4 shows four PPG signals, 401, 402, 403 and 404 obtained respectively from the sensors S1, S2, S3 and S4, depicted in FIG. 3, during five subsequent time segments T1, T2, T3, T4 and T5 that jointly form a time interval for PPG signal extraction. In FIG. 4, it is then assumed that a quality assessment is performed for the entire PPG signals 401, 402, 403 and 404. It is further assumed that the quality assessment reveals that PPG signals 401 and 402 are of bad quality, whereas PPG signals 403 and 404 are of good quality. Consequently, the PPG signals 403 and 404 are combined statically into multi-sensor PPG signal 405, e.g. through an averaged sum of these signals. The bad quality PPG signals 401 and 402 are removed and thus not used in the composition of the multi-sensor PPG signal 405. In the static multi-sensor PPG embodiment, illustrated by FIG. 4, no individual time segments of the signals are removed or selected for generation of the multi-sensor PPG signal 405. Although bad quality sub-region PPG signals 401 and 402 are removed, and good quality PPG signals 403 and 404 are maintained, it is still possible that bad quality segments that form part of the good quality PPG signals 403 and 404 are used in the multi-sensor PPG signal 405 and consequently negatively impact the accuracy of the multi-sensor PPG signal 405. It is also possible that good quality segments that form part of the bad quality PPG signals 401 and 402 are left unused, hence not exploiting all potential to compose an optimal multi-sensor PPG signal. The static multi-sensor PPG embodiment of the present invention, illustrated by FIG. 4 however is advantageous in that it requires limited processing to compose the multi-sensor PPG signal 405.

Figure 5:
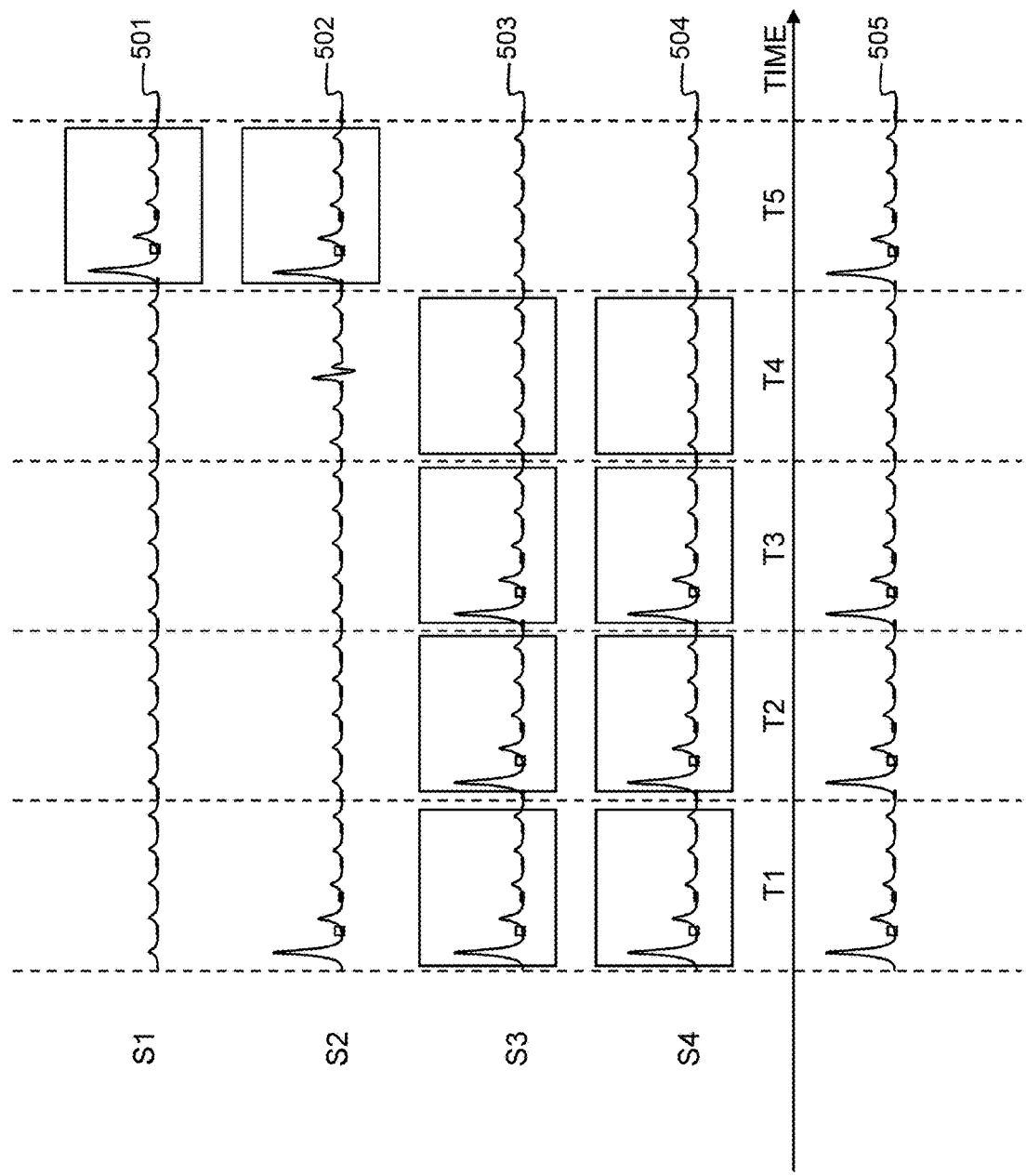
FIG. 5 illustrates the step of combining plural PPG signals into a multi-sensor PPG signal in embodiments of the computer-implemented method for direct PPG according to the present invention that implement dynamic multi-sensor PPG.

In a similar way, FIG. 5 shows four PPG signals, 501, 502, 503 and 504 obtained respectively from the sensors S1, S2, S3 and S4, depicted in FIG. 3, during five subsequent time segments T1, T2, T3, T4 and T5 that jointly form a time interval for PPG signal extraction. In FIG. 4, it is then assumed that a quality assessment is performed for the individual time segments T1, T2, T3, T4 and T5 of each of the PPG signals 501, 502, 503 and 504. It is further assumed that the quality assessment reveals that segments T1, T2, T3 and T4 of PPG signals 503 and 504 are of good quality, and segments T5 of PPG signals 501 and 502 are of good quality. All other segments are supposed to be of bad quality. Consequently, the good quality segments of the PPG signals 501, 502, 503 and 504 are dynamically combined to compose multi-sensor PPG signal 505. The segments T1 of PPG signals 503 and 504 are combined into segment S1 of multi-sensor PPG signal 505, e.g. through an averaged sum of these signals. Similarly, the segments T2 of PPG signals 503 and 504 are combined into segment T2 of multi-sensor PPG signal 505, the segments T3 of PPG signals 503 and 504 are combined into segment T3 of multi-sensor PPG signal 505, the segments T4 of PPG signals 503 and 504 are combined into segment T4 of multi-sensor PPG signal 505, and the segments T5 of PPG signals 501 and 502 are combined into segment T5 of multi-sensor PPG signal 505. The bad quality segments of PPG signals 501, 502, 503 and 504 are removed and thus not used in the composition of the multi-sensor PPG signal 505. The dynamic multi-sensor PPG embodiment illustrated by FIG. 5 is more processing intensive than the static multi-sensor PPG composition illustrated by FIG. 4, but brings the advantage that all good quality segments of all PPG signals obtained from plural sensors are used in order to generate a multi-sensor PPG signal 505 with enhanced accuracy and reliability. When compared with multi-sensor PPG signal 405, multi-sensor PPG signal 505 for instance contains the additional peak in time segment T5, as a result of using the good quality segments T5 of PPG signals 501 and 502.

Figure 6:
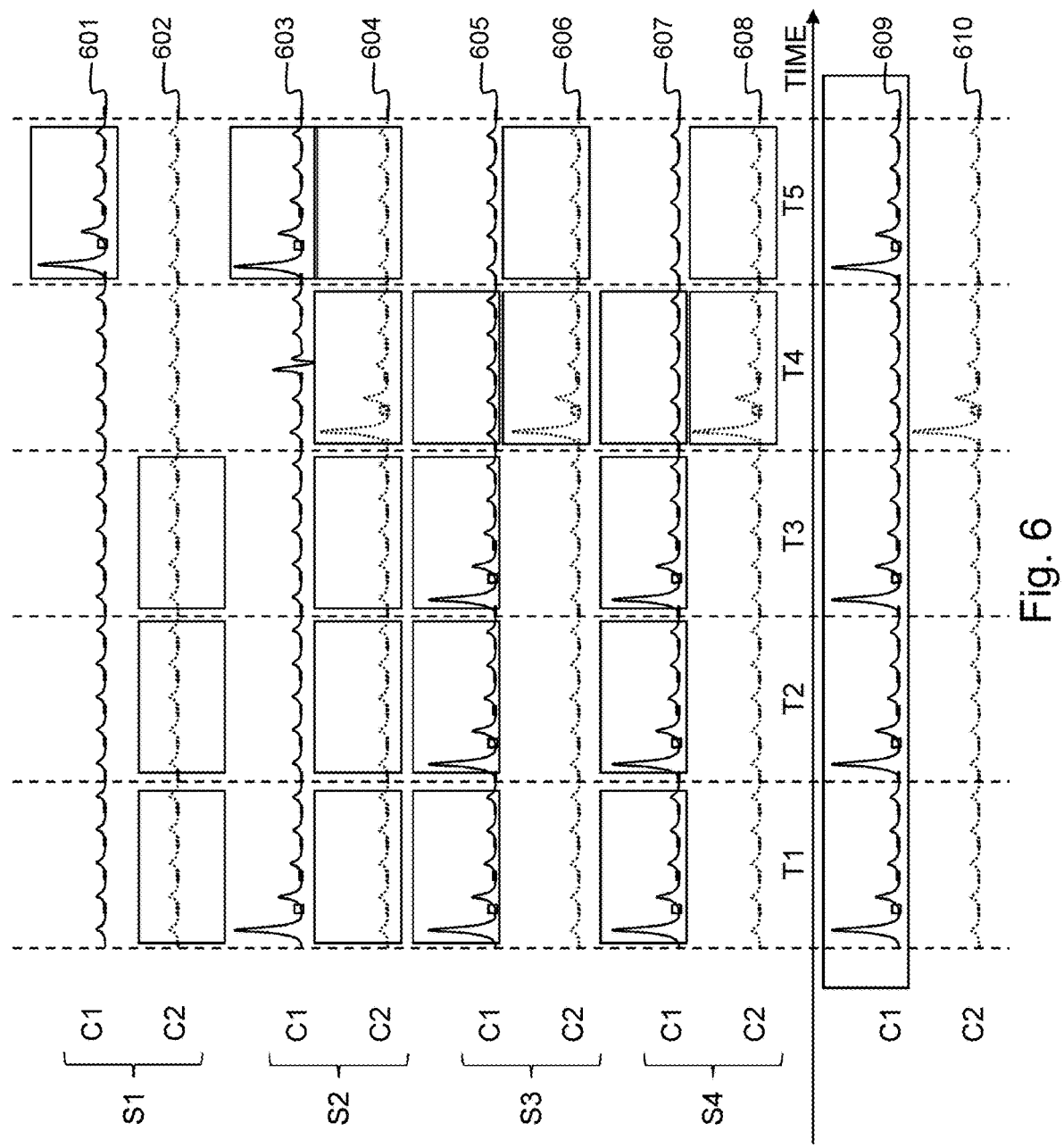
FIG. 6 illustrates the step of combining plural PPG signals into a multi-sensor PPG signal in embodiments of the computer-implemented method for direct PPG according to the present invention that implement dynamic multi-sensor PPG with color selection.

In a similar way, FIG. 6 shows eight PPG signals, 601, 602, 603, 604, 605, 606, 607 and 608 obtained respectively pairwise for a first color C1 and a second color C2 from the sensors S1, S2, S3 and S4, depicted in FIG. 3, during five subsequent time segments T1, T2, T3, T4 and T5 that jointly form a time interval for PPG signal extraction. From the first sensor S1, a first PPG signal 601 for color C1 and a second PPG signal 602 for color C2 are obtained. From the second sensor S2, a first PPG signal 603 for color C1 and a second PPG signal 604 for color C2 are obtained. From the third sensor S3, a first PPG signal 605 for color C1 and a second PPG signal 606 for color C2 are obtained. From the fourth sensor S4, a first PPG signal 607 for color C1 and a second PPG signal 608 for color C2 are obtained. In FIG. 6, it is then assumed that a quality assessment is performed for the individual time segments T1, T2, T3, T4 and T5 of each of the PPG signals 601-608. It is further assumed that for the first color C1, the quality assessment reveals that segments T1, T2, T3 and T4 of PPG signals 605 and 607 are of good quality, and segments T5 of PPG signals 601 and 603 are of good quality. All other segments in the C1 PPG signals 601, 603, 605 and 607 are supposed to be of bad quality. Consequently, the good quality C1 segments of the PPG signals 601, 603, 605 and 607 are dynamically combined to compose a multi-sensor PPG signal 609 for the first color C1. The segments T1 of PPG signals 605 and 607 are combined into segment T1 of multi-sensor PPG signal 609, e.g. through an averaged sum of these signals. Similarly, the segments T2 of PPG signals 605 and 607 are combined into segment T2 of multi-sensor PPG signal 609, the segments T3 of PPG signals 605 and 607 are combined into segment T3 of multi-sensor PPG signal 609, the segments T4 of PPG signals 605 and 607 are combined into segment T4 of multi-sensor PPG signal 609, and the segments T5 of PPG signals 601 and 603 are combined into segment T5 of multi-sensor PPG signal 609. The bad quality segments of PPG signals 601, 603, 605 and 607 are removed and thus not used in the composition of the multi-sensor PPG signal 609 for the first color C1. It is further assumed that for the second color C2, the quality assessment reveals that segments T1, T2 and T3 of PPG signals 602 and 604 are of good quality, and segments T4 and T5 of PPG signals 604, 606 and 608 are of good quality. All other segments in the C2 PPG signals 602, 604, 606 and 608 are supposed to be of bad quality. Consequently, the good quality C2 segments of the PPG signals 602, 604, 606 and 608 are dynamically combined to compose a multi-sensor PPG signal 610 for the second color C2. The segments T1 of PPG signals 602 and 604 are combined into segment T1 of multi-sensor PPG signal 610, e.g. through an averaged sum of these signals. Similarly, the segments T2 of PPG signals 602 and 604 are combined into segment T2 of multi-sensor PPG signal 610, the segments T3 of PPG signals 602 and 604 are combined into segment T3 of multi-sensor PPG signal 610, the segments T4 of PPG signals 604, 606 and 608 are combined into segment T4 of multi-sensor PPG signal 610, and the segments T5 of PPG signals 604, 606 and 608 are combined into segment T5 of multi-sensor PPG signal 610. The bad quality segments of PPG signals 602, 604, 606 and 608 are removed and thus not used in the composition of the multi-sensor PPG signal 610 for the second color C2. Thereafter, a quality assessment is made for the multi-sensor PPG signals 609 and 610 in order to select the best color, i.e. the color whose multi-sensor PPG signal has the best quality score according to some quality measure. In FIG. 6, it is assumed that the quality assessment reveals that multi-sensor PPG signal 609 has a better quality than multi-sensor PPG signal 610. As a result, the first color C1 is selected. The dynamic multi-sensor PPG embodiment with color selection illustrated by FIG. 6 is even more processing intensive, but brings the advantage that all good quality segments of all PPG signals obtained from multiple sensors are used and this for plural colors. Furthermore, the best color is selected in order to optimize the accuracy and reliability of the multi-sensor PPG signal without requiring the different colors to be synchronized.

Figure 7:
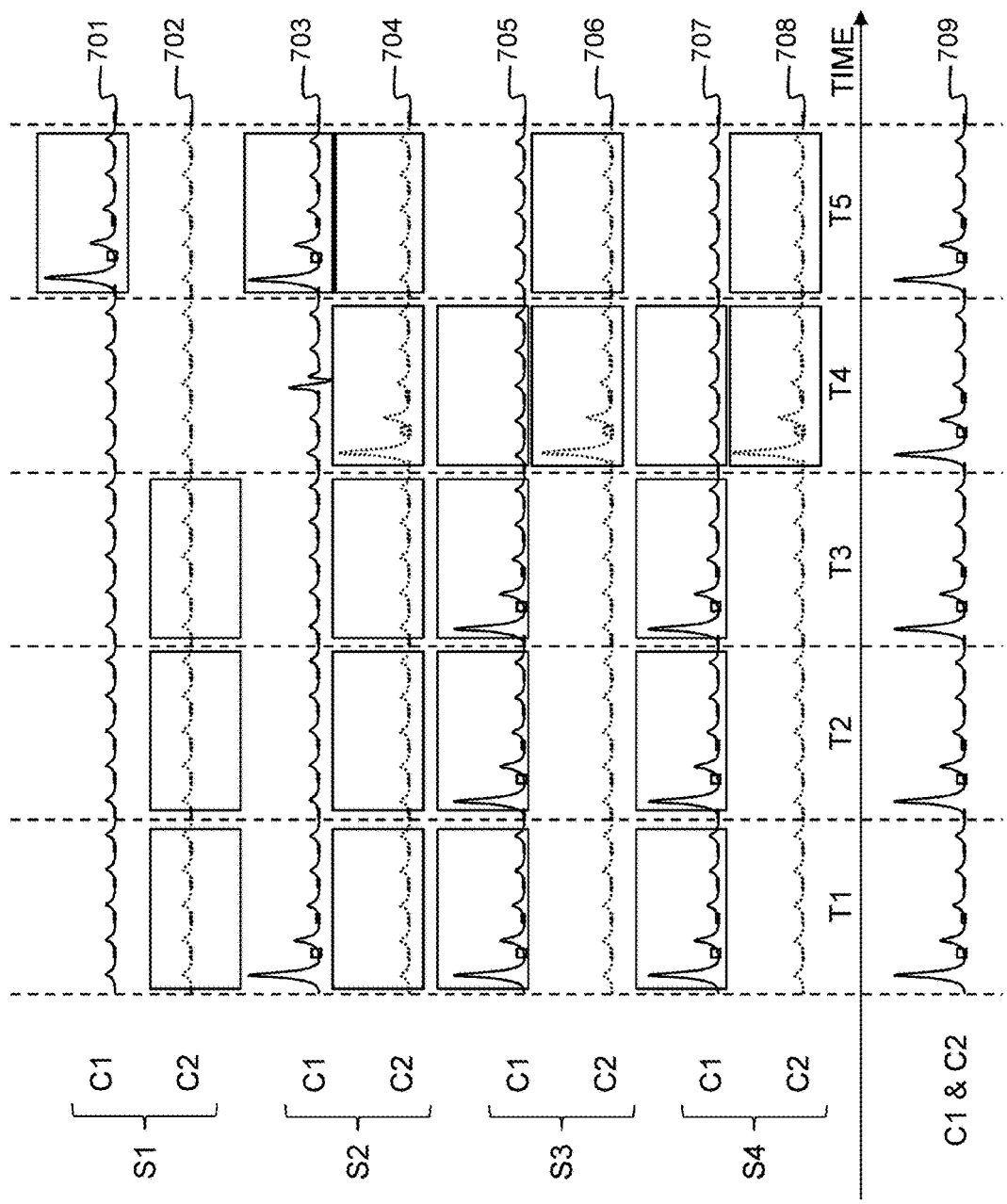
FIG. 7 illustrates the step of combining plural PPG signals into a multi-sensor PPG signal in embodiments of the computer-implemented method for direct PPG according to the present invention that implement dynamic multi-sensor multi-color PPG.

In a similar way, FIG. 7 shows eight PPG signals, 701, 702, 703, 704, 705, 706, 707 and 708 obtained respectively pairwise for a first color C1 and a second color C2 from the sensors S1, S2, S3 and S4, depicted in FIG. 3, during five subsequent time segments T1, T2, T3, T4 and T5 that jointly form a time interval for PPG signal extraction. From the first sensor S1, a first PPG signal 701 for color C1 and a second PPG signal 702 for color C2 are obtained. From the second sensor S2, a first PPG signal 703 for color C1 and a second PPG signal 704 for color C2 are obtained. From the third sensor S3, a first PPG signal 705 for color C1 and a second PPG signal 706 for color C2 are obtained. From the fourth sensor S4, a first PPG signal 707 for color C1 and a second PPG signal 708 for color C2 are obtained. In FIG. 7, it is then assumed that a quality assessment is performed for the individual segments T1, T2, T3, T4 and T5 of each of the sub-region PPG signals 701-708. It is further assumed that for the first color C1, the quality assessment reveals that segments T1, T2, T3 and T4 of PPG signals 705 and 707 are of good quality, and segments T5 of PPG signals 701 and 703 are of good quality. All other segments in the C1 PPG signals 701, 703, 705 and 707 are supposed to be of bad quality. It is further assumed that for the second color C2, the quality assessment reveals that segments T1, T2 and T3 of PPG signals 702 and 704 are of good quality, and segments T4 and T5 of PPG signals 704, 706 and 708 are of good quality. All other segments in the C2 PPG signals 702, 704, 706 and 708 are supposed to be of bad quality. The good quality segments of plural colors that are temporarily corresponding and that are supposed to be synchronised are then dynamically combined into a single multi-color multi-sensor PPG signal 709. Thus, the segments T1 of PPG signals 702, 704, 705 and 707 are combined into segment T1 of multi-sensor PPG signal 709, e.g. through an averaged sum of these signals. Similarly, the segments T2 of PPG signals 702, 704, 705 and 707 are combined into segment T2 of multi-sensor PPG signal 709, the segments T3 of PPG signals 702, 704, 705 and 707 are combined into segment T3 of multi-sensor PPG signal 709, the segments T4 of PPG signals 704, 705, 706, 707 and 708 are combined into segment T4 of multi-sensor PPG signal 709, and the segments T5 of PPG signals 701, 703, 704, 706 and 708 are combined into segment T5 of multi-sensor PPG signal 709. The bad quality segments of PPG signals 701-708 are removed and thus not used in the composition of the multi-sensor PPG signal 709. The dynamic multi-color multi-sensor PPG embodiment illustrated by FIG. 7 is even more processing intensive and requires synchronization between the colors C1 and C2, but it brings the advantage that all good quality segments of all PPG signals across all sensors and all colors are combined. This way, a PPG signal 709 is composed with optimal accuracy and reliability. Compared with the embodiment illustrated by FIG. 6, it is noticed for instance that the multi-color multi-sensor PPG signal 709 obtained through dynamic combination of sensors and colors also contains the peak in segment T4, whereas this peak remains absent in the multi-sensor PPG signal 609 obtained through dynamic combination of sensors with color selection.

Figure 8:
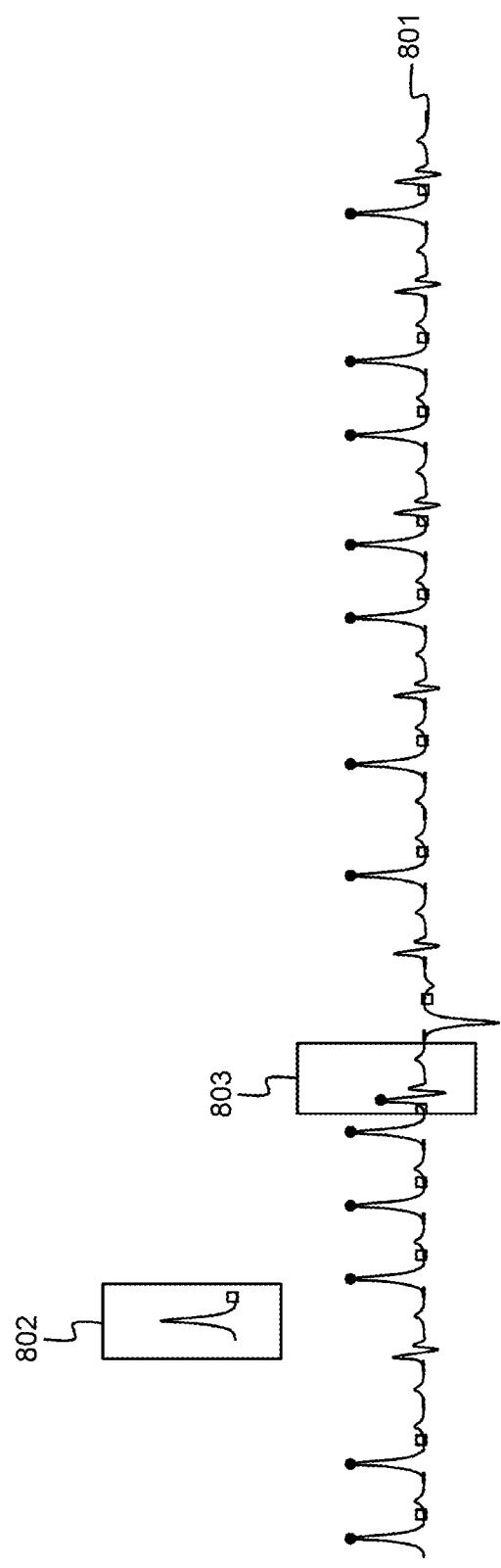
FIG. 8 illustrates the step of peak detection in embodiments of the computer-implemented method for direct PPG according to the present invention that implement template based peak selection.

FIG. 8 illustrates a possible implementation of the peak detection step 106 in FIG. 1. In the multi-sensor PPG signal 801, peaks are detected, e.g. by comparing the signal strength with the average signal strength. Detected peaks in multi-sensor PPG signal 801 are marked with a dot. These peaks are then windowed and the windowed peaks are averaged to generate a peak template 802, i.e. a model peak. Thereafter, each detected peak is correlated with the peak template 802. Peaks for which the correlation exceeds a certain correlation threshold are maintained. Peaks for which the correlation stays below the correlation threshold, like for instance 803 in FIG. 8, are removed. With the remaining peaks, the steps of averaging to generate a peak template, correlating to identify peaks that are kept and peaks that are dropped, are iteratively repeated until a stable situation is reached wherein no peaks are dropped anymore.

Figure 9:
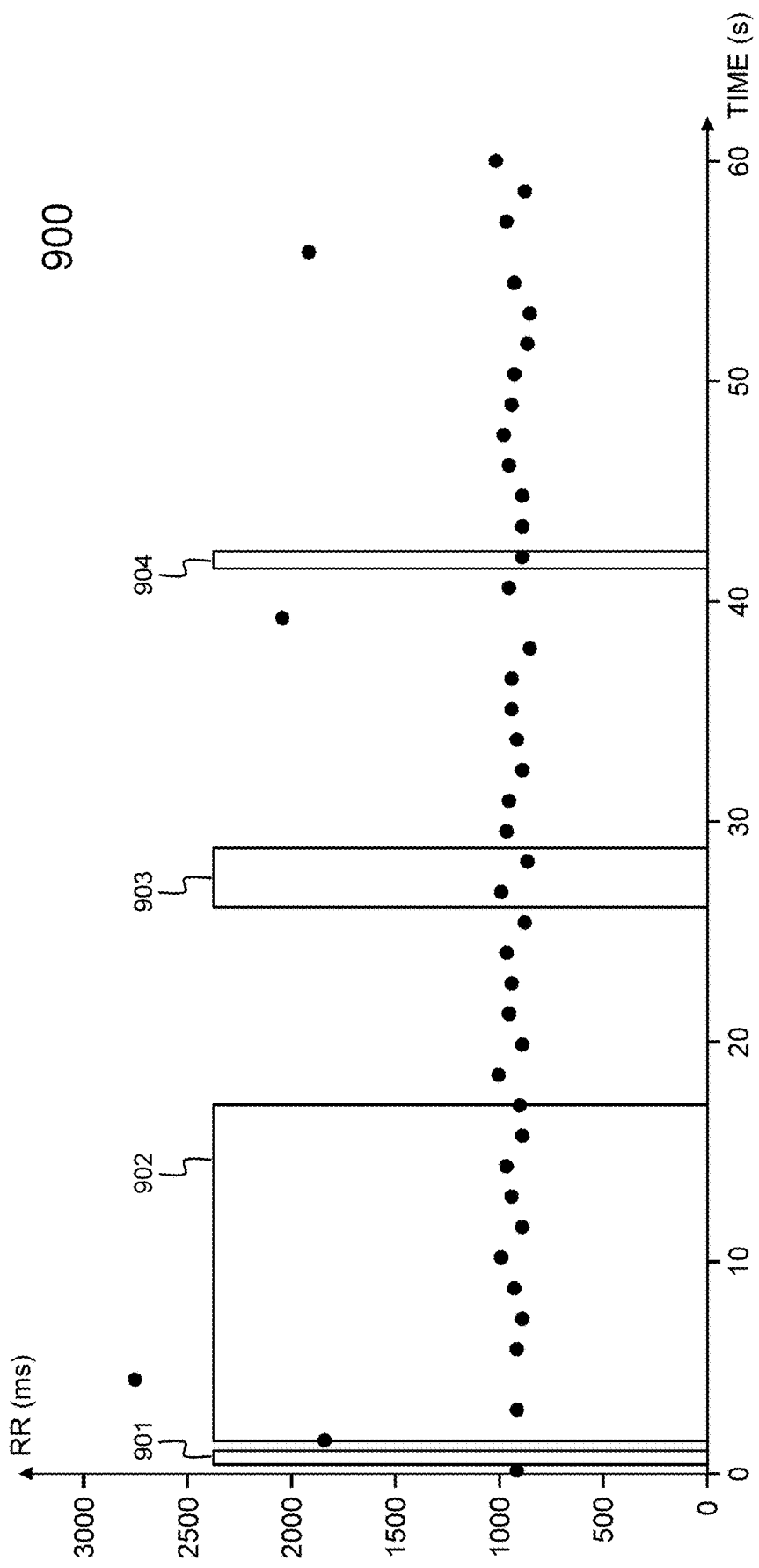
FIG. 9 illustrates the step of RR-tachogram extraction in embodiments of the computer-implemented method for direct PPG according to the present invention.

FIG. 9 illustrates a possible implementation of the RR-tachogram extraction step 107 in FIG. 1. The RR-tachogram 900 has the time as horizontal axis and the time difference between subsequent peaks in the multi-sensor PPG signal as vertical axis. Hence, the RR-tachogram shows the variability in the peak rate, i.e. the variability in the heartrate in case the peaks in the multi-sensor PPG signal represent heart pulses of a monitored person. The reliability of the extracted RR-tachogram may be improved by performing a quality analysis of the multi-sensor PPG signal. This quality analysis may be done using a quality assessment technique similar to the one described here above, i.e. based on wavelet transforming and neural network analysis, but the skilled person will appreciate that other quality analysis techniques may be applied as well to identify good quality portions and bad quality portions in the multi-sensor PPG signal. RR-intervals that are located entirely or partially within a bad quality portion of the multi-sensor PPG signal, like 901, 902, 903 and 904 in FIG. 9. This way, a processed, more reliable RR-tachogram is obtained. From the RR-tachogram, the variability in the peak rate can be determined. If this variability exceeds certain thresholds, corresponding atrial fibrillation risk score values may be reported to the monitored person or his physician.

Figure 10:
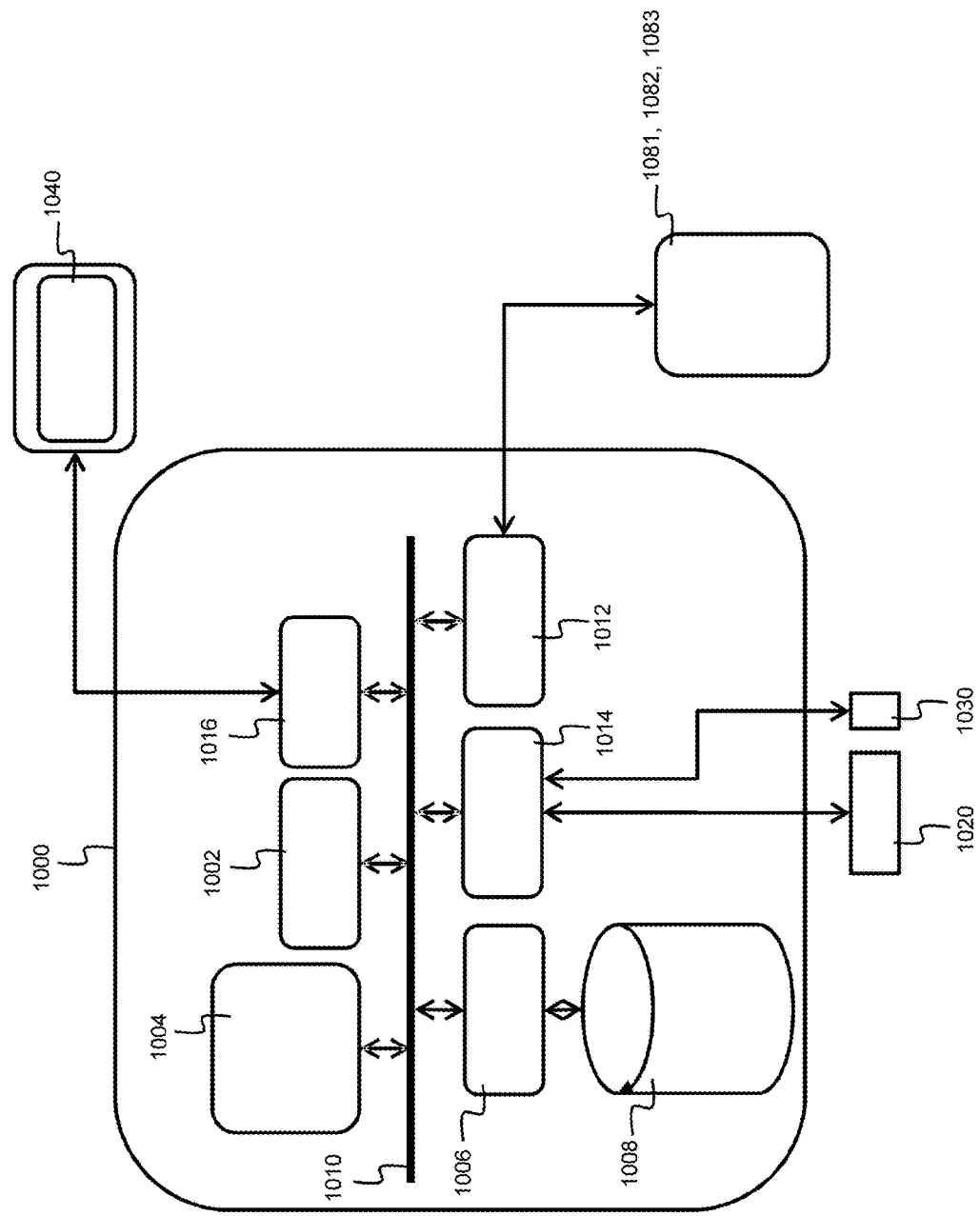
FIG. 10 illustrates a suitable computing system 1000 for realizing methods and devices according to embodiments of the invention.

FIG. 10 shows a suitable computing system 1000 according to an embodiment of the invention. Computing system 1000 is suitable for implementing embodiments of the method for direct PPG in accordance with the present invention. Computing system 1000 may in general be formed as a suitable general-purpose computer and comprise a bus 1010, a processor 1002, a local memory 1004, one or more optional input interfaces 1014, one or more optional output interfaces 1016, a communication interface 1012, a storage element interface 1006 and one or more storage elements 1008. Bus 1010 may comprise one or more conductors that permit communication among the components of the computing system 1000. Processor 1002 may include any type of conventional processor or microprocessor that interprets and executes programming instructions. Local memory 1004 may include a random access memory (RAM) or another type of dynamic storage device that stores information and instructions for execution by processor 1002 and/or a read only memory (ROM) or another type of static storage device that stores static information and instructions for use by processor 1002. Input interface 1014 may comprise one or more conventional mechanisms that permit an operator or user to input information to the computing device 1000, such as a keyboard 1020, a mouse 1030, a pen, voice recognition and/or biometric mechanisms, a camera, etc. Output interface 1016 may comprise one or more conventional mechanisms that output information to the operator or user, such as a display 1040, etc. Communication interface 1012 may comprise any transceiver-like mechanism such as for example one or more Ethernet interfaces that enables computing system 1000 to communicate with other devices and/or systems, for example with other computing devices 1081, 1082, 1083. The communication interface 1012 of computing system 1000 may be connected to such another computing system by means of a local area network (LAN) or a wide area network (WAN) such as for example the internet. Storage element interface 1006 may comprise a storage interface such as for example a Serial Advanced Technology Attachment (SATA) interface or a Small Computer System Interface (SCSI) for connecting bus 1010 to one or more storage elements 1008, such as one or more local disks, for example SATA disk drives, and control the reading and writing of data to and/or from these storage elements 1008. Although the storage elements 1008 above is described as a local disk, in general any other suitable computer-readable media such as a removable magnetic disk, optical storage media such as a CD or DVD, -ROM disk, solid state drives, flash memory cards, . . . could be used. It is noticed that the entire method according to the present invention can be executed centralized, e.g. on a server in a management centre or in a cloud system, or it can be partially executed on a remote electronic device, e.g. worn by the user, and partially on a central server. Computing system 1000 could thus correspond to the processing system available centrally or the processing system available in the electronic device.

Although the present invention has been illustrated by reference to specific embodiments, it will be apparent to those skilled in the art that the invention is not limited to the details of the foregoing illustrative embodiments, and that the present invention may be embodied with various changes and modifications without departing from the scope thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein. In other words, it is contemplated to cover any and all modifications, variations or equivalents that fall within the scope of the basic underlying principles and whose essential attributes are claimed in this patent application. It will furthermore be understood by the reader of this patent application that the words "comprising" or "comprise" do not exclude other elements or steps, that the words "a" or "an" do not exclude a plurality, and that a single element, such as a computer system, a processor, or another integrated unit may fulfil the functions of several means recited in the claims. Any reference signs in the claims shall not be construed as limiting the respective claims concerned. The terms "first", "second", third", "a", "b", "c", and the like, when used in the description or in the claims are introduced to distinguish between similar elements or steps and are not necessarily describing a sequential or chronological order. Similarly, the terms "top", "bottom", "over", "under", and the like are introduced for descriptive purposes and not necessarily to denote relative positions. It is to be understood that the terms so used are interchangeable under appropriate circumstances and embodiments of the invention are capable of operating according to the present invention in other sequences, or in orientations different from the one(s) described or illustrated above.

The invention claimed is:

1. A computer-implemented method for direct photoplethysmography or direct PPG comprising:
   obtaining during a time interval wherein a continuous direct PPG measurement is carried out, plural PPG signals by respective plural sensors in a wearable device, said plural sensors corresponding to plural cameras or plural photodiodes or a combination thereof; and
   combining said plural PPG signals to thereby obtain a multi-sensor PPG signal,
   wherein said method for direct PPG comprises:
   segmenting said plural PPG signals identically such that for each segment in a PPG signal obtained by a sensor of the plural sensors temporally corresponding segments exist in the PPG signals obtained by other sensors of the plural sensors;
   processing each PPG signal of said plural PPG signals to identify good quality segments of said PPG signal wherein a quality measure of said PPG signal is above a threshold and bad quality segments of said PPG signal wherein said quality measure of said PPG signal is below said threshold;
   removing said bad quality segments from each PPG signal of said plural PPG signals; and
   combining temporally corresponding good quality segments from each PPG signal of said plural PPG signals to obtain said multi-sensor PPG signal.

2. The computer-implemented method for direct PPG according to claim 1, wherein said good quality segments comprise non-inverted segments and inverted segments and said processing of each PPG signal further comprises identifying said inverted segments and reverting said inverted segments.

3. The computer-implemented method for direct PPG according to claim 2, wherein said neural network is further trained to identify said inverted segments.

4. The computer-implemented method for direct PPG according to claim 1, wherein said processing of each PPG signal comprises:
- wavelet transforming said PPG signal to obtain a wavelet transformed PPG signal; and
- supplying said wavelet transformed PPG signal to a neural network trained to identify good quality segments of said PPG signal and bad quality segments of said PPG signal.

5. The computer-implemented method for direct PPG according to claim 1, comprising:
- obtaining said PPG signals for multiple colors;
- generating for each color from the PPG signals obtained from plural sensors for said color a multi-sensor PPG signal by combining temporally corresponding good quality segments of said plural PPG signals obtained for said color, resulting in plural multi-sensor PPG signals for respective colors.

6. The computer-implemented method for direct PPG according to claim 5, further comprising:
- determining a quality measure for each one of said colors; and
- selecting amongst said plural multi-sensor PPG signals the multi-sensor PPG signal for the color with highest quality measure.

7. The computer-implemented method for direct PPG according to claim 5, further comprising:
- determining a quality measure for each one of said colors; and
- combining multi-sensor PPG signals for plural colors into a multi-color multi-sensor PPG signal.

8. The computer-implemented method for direct PPG according to claim 7, further comprising:
- obtaining during said time interval plural PPG signals for respective colors and respective sensors;
- processing each PPG signal of said plural PPG signals to identify good quality segments of said PPG signal wherein a quality measure of said PPG signal is above a threshold and bad quality segments of said PPG signal wherein said quality measure of said PPG signal is below said threshold;
- removing said bad quality segments from each PPG signal of said plural PPG signals; and
- combining temporally corresponding good quality segments of said plural PPG signals to obtain said multi-color multi-sensor PPG signal.

9. The computer-implemented method for direct PPG according to claim 5, further comprising:
- subdividing at least one of said sensors in multiple sub-regions, each sub-region of said sub-regions covering multiple pixels;
- obtaining during said time interval for the at least one of said sensors plural PPG signals for respective different sub-regions of said sensor; and
- combining said plural PPG signals to thereby obtain a multi-color multi-sensor multi-region PPG signal.

10. The computer-implemented method for direct PPG according to claim 1, further comprising:
- subdividing at least one of said plural sensors in multiple sub-regions, each sub-region of said sub-regions covering multiple pixels;
- obtaining during said time interval for the at least one of said sensors plural PPG signals for respective different sub-regions of said sensor; and
- combining said plural PPG signals to thereby obtain a multi-sensor multi-region PPG signal.

11. The computer-implemented method for direct PPG according to claim 1, further comprising locking settings of one or more of said sensors during said time interval, said settings at least comprising:
- diaphragm;
- sensor setting for light sensitivity; and
- light exposure time.

12. The computer-implemented method for direct PPG according to claim 1, further comprising detecting peaks in said multi-sensor PPG signal, and thereto comprising:
- detecting initial peaks in said multi-sensor PPG signal;
- windowing said initial peaks in said multi-sensor PPG signal to thereby generate windowed initial peaks;
- averaging said windowed initial peaks in said multi-sensor PPG signal to thereby generate a peak template;
- correlating said initial peaks with said peak template;
- keeping initial peaks for which a correlation measure indicative for the correlation with said peak template exceeds a correlation threshold as peaks in said multi-sensor PPG signal; and
- removing initial peaks for which said correlation measure indicative for the correlation with said peak template does not exceed said correlation threshold from said multi-sensor PPG signal.

13. The computer-implemented method for direct PPG according to claim 12, further comprising:
- extracting an RR-tachogram by determining a time difference between subsequent peaks in said multi-sensor PPG signal.

14. The computer-implemented method for direct PPG according to claim 13, further comprising:
- processing said multi-sensor PPG signal to identify good quality segments of said multi-sensor PPG signal wherein a quality measure of said multi-sensor PPG signal is above a threshold and bad quality segments of said multi-sensor PPG signal wherein said quality measure of said multi-sensor PPG signal is below said threshold;
- removing peaks within said bad quality segments from said multi-sensor PPG signal before extracting said RR-tachogram; and
- removing from said RR-tachogram the RR-tachogram intervals located totally or partially within said bad quality segments of said multi-sensor PPG signal.

15. The computer-implemented method for direct PPG according to claim 13, further comprising:
- determining a variability in said time difference between subsequent peaks; and
- determining from said variability an atrial fibrillation risk score.

16. A computer program product comprising computer-executable instructions for performing the method according to claim 1 when the program is run on a computer.

17. A computer readable storage medium comprising the computer program product according to claim 16.

18. A data processing system programmed for carrying out the method according to claim 1.

* * * * *